US 6,693,277 B2

(12) United States Patent
Cowan et al.

(10) Patent No.: US 6,693,277 B2
(45) Date of Patent: *Feb. 17, 2004

(54) DETECTION OF SUBMICRON SCALE CRACKS AND OTHER SURFACE ANOMALIES USING POSITRON EMISSION TOMOGRAPHY

(75) Inventors: Thomas E. Cowan, Livermore, CA (US); Richard H. Howell, Livermore, CA (US); Carlos A. Colmenares, Alamo, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 317 days.

(21) Appl. No.: 09/224,748

(22) Filed: Jan. 4, 1999

(65) Prior Publication Data
US 2001/0006215 A1 Jul. 5, 2001

(51) Int. Cl.⁷ .............................................. G01T 1/169
(52) U.S. Cl. ....................................... 250/303
(58) Field of Search ......................................... 250/303

(56) References Cited

U.S. PATENT DOCUMENTS 3,924,125 A * 12/1975 Murray ....................... 250/303
4,983,841 A * 1/1991 Stewart et al. ............ 250/358.1
5,453,615 A * 9/1995 Mis ............................ 250/303

FOREIGN PATENT DOCUMENTS

DE         268 526 A1 *  5/1989   ................ 250/303
FR         2 389 126    * 11/1978   ................ 250/303

OTHER PUBLICATIONS

Richard S. Arthur, abstract of application No. [03/] 206,829 filed Jan. 19, 1951 for "Crack Detection Method." Published at 655 Official Gazette 1177, Feb. 1952.*

* cited by examiner

Primary Examiner—Constantine Hannaher
(74) Attorney, Agent, or Firm—L. E. Carnahan; Alan H. Thompson

(57) ABSTRACT

Detection of submicron scale cracks and other mechanical and chemical surface anomalies using PET. This surface technique has sufficient sensitivity to detect single voids or pits of sub-millimeter size and single cracks or fissures of millimeter size; and single cracks or fissures of millimeter-scale length, micrometer-scale depth, and nanometer-scale length, micrometer-scale depth, and nanometer-scale width. This technique can also be applied to detect surface regions of differing chemical reactivity. It may be utilized in a scanning or survey mode to simultaneously detect such mechanical or chemical features over large interior or exterior surface areas of parts as large as about 50 cm in diameter. The technique involves exposing a surface to short-lived radioactive gas for a time period, removing the excess gas to leave a partial monolayer, determining the location and shape of the cracks, voids, porous regions, etc., and calculating the width, depth, and length thereof. Detection of 0.01 mm deep cracks using a 3 mm detector resolution has been accomplished using this technique.

12 Claims, 2 Drawing Sheets

DETECTION OF SUBMICRON SCALE CRACKS AND OTHER SURFACE ANOMALIES USING POSITRON EMISSION TOMOGRAPHY

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to detection of cracks, etc., in surfaces, particularly to detection of submicron scale cracks and other surface anomalies, and more particularly to the detection of cracks and other mechanical and chemical surface anomalies using Positron Emission Tomography (PET).

The detection of cracks, voids, and porous regions in metal parts is a generic problem in the field of manufacturing and long-term storage of such parts. This is of particular concern with special significance to the maintenance of the nuclear stockpile. Present radiographic techniques are prone to miss small cracks, and similar features in a general survey, and are difficult to apply in some circumstances. For example, the minimum crack width detectable by computed tomography is about 40 micrometers, or by neutron radiography is about 1 millimeter. Microscopic visual inspection suitable for very small features is limited by its narrow field of view to scanning small areas only. These prior above-identified techniques are among those used routinely for detecting cracks, voids, and fatigue-related failure of mechanical and structural components, ranging from airplane wings to bridge abutments.

PET is a known medical imaging technology. By recognition that PET can be utilized in fields other than medical, the present invention enabled this known medical technology to be applied so as to enable the detection of submicron scale cracks and other mechanical and chemical surface anomalies. Thus the present invention involves the application of PET to detect the presence of cracks and similar mechanical features on surfaces of metallic or mechanical parts, or other materials, and to locate those features with millimeter spatial resolution. It was also recognized that PET technology can be applied to detect very small features in a scanning mode suitable for application to surveillance of the nuclear stockpile, for example, and other engineering applications. In carrying out the method of the present invention, a radioactive gas is directed onto the surface of a part to be inspected, the gas is pumped away leaving a fraction of a monolayer of gas residue on the surface of the port, after which coincident gamma-rays are detected to determine the location and shape of the cracks, voids, porous regions, etc., and calculating the width, depth, and length thereof. Detection of 0.01 $\mu$m wide by 10 $\mu$m deep cracks is possible with the method of the present invention.

SUMMARY OF THE INVENTION

It is an object of the present invention to detect submicron scale cracks and other mechanical and chemical surface anomalies.

A further object of the invention is to detect submicron scale cracks in metallic or other material parts using PET.

A further object of the invention is to provide an application of PET to detect surface regions of differing chemical reactivity.

Another object of the invention is to utilize PET in a scanning or survey mode to simultaneously detect mechanical and chemical features over large interior or exterior surface areas of parts as large as about 50 cm in diameter.

Another object of the invention is to provide a method for detecting cracks and weld integrity on the interior surface of a spherical part using any positron-emitting radioisotopes in PET.

Another object of the invention is to provide a method which utilizes any type of position-sensitive gamma-ray detectors for surface feature detection and characterization by PET.

Another object of the invention is to provide an application of PET to detection of submicron scale cracks and other mechanical and chemical surface anomalies using positron-emitting radioisotopes which can be delivered to the surface via gaseous residue by solution or fluid applied to the surface, by aerosol sprayed on the surface, by high-pressure gas, solution, fluid, or spray on the surface; or by producing positron-emitting radioisotopes on the surface by activation of a pre-existing material (e.g., an oxide layer).

Other objects and advantages of the present invention will become apparent from the following description and accompanying drawings. Basically, the present invention involves PET applied to detect submicron scale cracks and other mechanical and chemical surface anomalies. The method or technique of this invention has sufficient sensitivity to detect single voids or pits of submillimeter size, and single cracks or fissures of millimeter-scale length, micrometer-scale depth, and nanometer-scale width. The techniques or method of this invention can also be applied to detect surface regions of differing chemical reactivity, as well as in a scanning or survey mode to detect features over large interior and exterior surface areas. Basically, the method or technique involves exposing a surface to short-lived radioactive material for a time period; removing the excess radioactive material to leave a surface residue; determining the location and shape of the cracks, voids, porous regions, etc., due to the "bright" spots caused by increased surface areas of the cracks, etc.; and calculating the width, depth, and length thereof. Cracks as shallow as 10 $\mu$m and wide as 0.01 $\mu$m are detectable with this method.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

The present invention involves an application of PET to the detection of submicron scale cracks and other mechanical and chemical surface anomalies. PET is a known medical imaging technology, and this technology is here applied to detect very small features in a scanning type mode, for example, suitable for application to surveillance of parts, particularly parts in storage, such as the nuclear stockpile, as well as other engineering applications, such as non-destructive evaluation (NDE) of surface quality or joint integrity in manufacturing. The method of this invention requires the application of a positron-emitting radioactive isotope to the surface being interrogated, and imaging the subsequent 511 keV annihilation gamma-rays to reconstruct the source distribution on the surface. Cracks and similar surface features have more surface area to which the radioisotope may adhere than a smooth featureless surface, and therefore show up as regions of increased source activity. Determining the location and shape of the feature is limited by the spatial resolution of the detector (typically about a few mm), and the distance into the material which the positron travels before annihilating (about 0.1 mm for a 1 MeV positron in Pu). The sensitivity of the technique to cracks and similar features relies on the deposition of the radioactive positron-emitter on the additional surface exposed by the feature, and is proportional to the increase in the area compared to a featureless surface.

The particular features encompassed by the present invention involve: (1) application of PET to detect mechanical surface features (e.g., cracks, pores, voids, fissures); (2) application of PET to detect chemical surface features (regions of different reactivity to tracer material); (3) use of any positron-emitting radioisotopes for surface feature detection and characterization by PET; (4) use of any type of position-sensitive gamma-ray detectors for surface feature detection and characterization by PET; (5) means of delivery of positron emitter to surface via gaseous residue, which include delivery by solution or fluid applied to the surface, delivery by aerosol sprayed on the surface, delivery by high-pressure gas, solution, fluid, or spray; and (6) means of producing positron-emitting radioisotopes on the surface by activation of a pre-existing material (e.g., an oxide layer).

Figure 1:
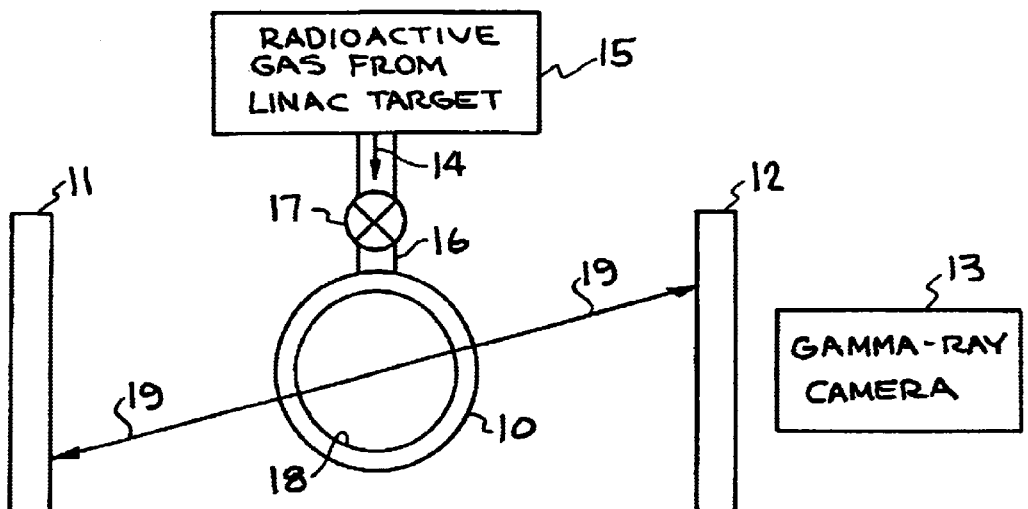
FIG. 1 illustrates an evacuated sphere containing a gas residue placed between two position-sensitive gamma-ray detectors, in accordance with the present invention.
Figure 2A:
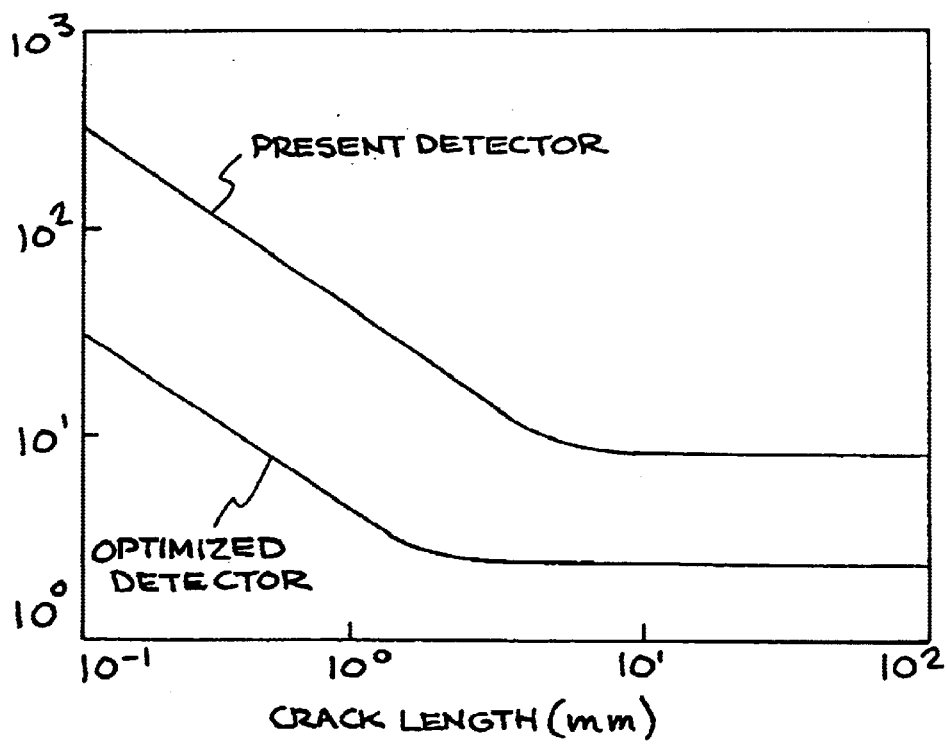
FIG. 2A graphically illustrates single-crack sensitivity using detection by Positron Emission Tomography.
Figure 2B:
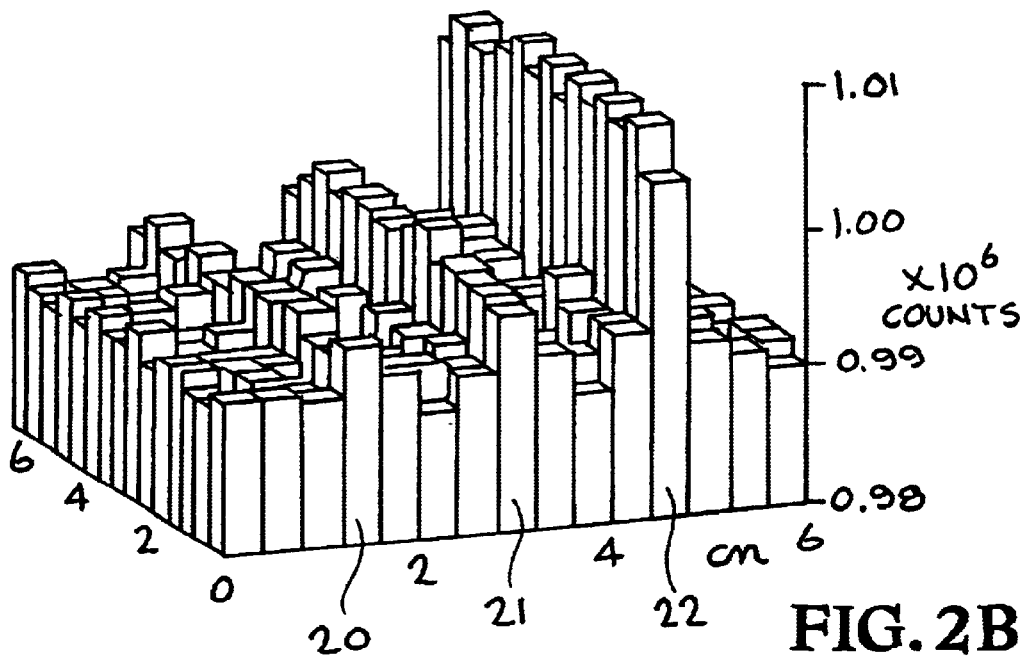
FIGS. 2B and 2C illustrate by Monte Carlo calculation the depth, width, and length of three cracks using the method of the present invention.

An application of the method or technique of the present invention to detecting cracks and weld integrity on the interior surface of a spherical part (e.g., a Pu pit) is illustrated in FIGS. 1, 2A, and 2B, and demonstrates the basic principal and sensitivity. FIG. 1 illustrates a sphere 10 placed between two position-sensitive gamma-ray detectors 11 and 12 in which the back-to-back 511 keV annihilation gamma-rays are detected and recorded by a gamma-ray Camera, generally indicated at 13, the detectors 11 and 12 having a 50 cm diameter, 3 mm resolution. The sphere 10 is first evacuated, and then radioactive gas indicated at arrow 14; e.g., carbon dioxide labeled with C-11, which has a 20.5 minute half-life, is injected into the sphere 10, such as radioactive gas 14 being supplied from a Linac target 15 via a tube 16 and valve 17, as shown in FIG. 1. The gas is pumped away via tube 16 and valve 17, leaving a fraction of a monolayer of gas residue on the interior surface 18 of sphere 10. The coincident gamma rays, indicated by arrows 19, are detected by detectors 11 and 12 and the source distribution on the emitting surface 18 is reconstructed by back projecting onto planes through the sphere 10.

FIG. 2A shows a calculation of the sensitivity of the method, identified as optimized detector (lower line) to an isolated, single crack, compared to a present detector (upper line). Here the method of the present invention (optimized detector) utilized a radioactive gas of $^{11}CO_2$, 1 mCi/cm$^2$ (10 ppm), with a 1 hour exposure time, and a 10 nm crack width was detected.

Figure 2C:
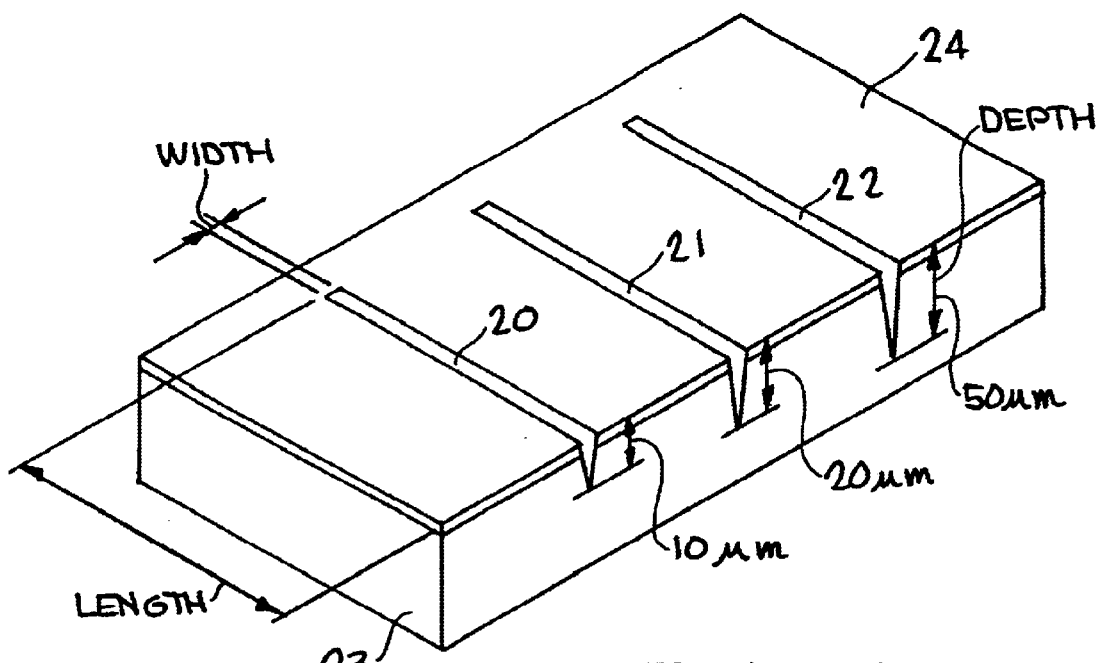

FIGS. 2B and 2C show an experimental verification of the method of the present invention involving three isolated cracks 20, 21, and 22 in a part 23 having a $CO_2$ surface layer 24. The cracks are modeled, each 10 nm wide (wide enough to allow gas to diffuse into the interior surface of the crack), of the same length, and respectively 10, 20, and 50 $\mu$m deep. Each crack is several mm long (greater than the assumed detector resolution of 3 mm). The gaseous positron emitter (the $CO_2$ layer 24) is shown to partially coat the surface of the part 23 and down into the cracks 20, 21, and 22. A Monte Carlo calculation shows the events detected per 4 mm×4 mm bin in the back-projected plane of the emitting surface 24. The quantity of data assumes a 1 hour collection time and realistic counting rates, gamma-ray attenuation, and detector resolution. It is seen that cracks as shallow as 10 $\mu$m are detectable. With improved detectors, smaller cracks of about 1 $\mu$m depth should be resolvable. If the crack length is shorter than the detector resolution, the crack must be deeper to have sufficient surface area to be detected. This is denoted in the single-crack sensitivity plot of FIG. 2A.

The sensitivity is determined by the counting statistics and the image analysis. In this example, only simple binning of the image was performed. More sophisticated "crack finding" algorithms and better detectors will lead to correspondingly greater sensitivity. The counting statistics appear to be limited primarily by the detector data acquisition rate and not by the fractional source coverage. In this example, the gas was assumed to cover only $10^{-5}$ of a single monolayer, corresponding to an activity concentration of only about 1 m Ci/cm$^2$ of $^{11}CO_2$. The use of short-lived isotopes (such as $^{11}C$, $^{13}N$, $^{15}O$, $^{18}F$, etc.) limits the long-term exposure of the part and eliminates the need for post-examination surface cleaning, rendering the technique essentially non-destructive. The radioactive material may be applied to the external surface of the sphere 10 in FIG. 1, or another part configuration, in a gaseous form or as a solution applied to the surface and wiped off, or as a solution injected at high pressure, as a mist or aerosol sprayed onto the surface, or by any other technique which produces a partial surface coating. Delivery of the material to the surface and its adherence there may be in part controlled by the molecular form of the isotope (e.g., $CO_2$, $H_2O$, $CO$, $O_2$, $N_2$, $NO_x$, $NH_3$, $O_3$, etc.) By appropriate selection, surface regions of differing chemical reactivity may also be detected (as opposed to mechanical features discussed above).

In addition, the PET method of this invention can be a useful technique for interrogating surface features in many radioactive materials, as well as nonradioactive, because it involves the coincidental detection of two very specific (i.e., 511 keV) gamma-rays. If the material under interrogation is not a positron emitter itself, its own radiation field of single or multiple gamma-rays will be distinguishable from the PET trace materials' positron annihilations. Depending on the level of activity, this will add a relatively small chance coincidence component which can be corrected in the data processing and will not significantly affect the image quality.

It has thus been shown that the present invention provides for detection of submicron scale cracks and other mechanical and chemical surface anomalies. It can be utilized to interrogate the interior of small metallic parts and/or the exterior of the parts, as well as detecting mechanical or chemical features over large interior or exterior surface areas of parts as large as about 50 cm in diameter. The size restriction may be significantly extended by improved detector developments.

Numerous uses of the invention include screening parts from nuclear weapons stockpile for cracks, surface pitting, porosity, and interfacial delamination or corrosion; inspecting the interior of spherical parts such as nuclear pit, for incipient or fully developed cracks while in storage or prior to redeployment; determining the volume of exterior surface cracks of pits; inspecting and certifying welds of reprocessed parts; and qualifying new advanced manufacturing and processing techniques for surface quality and integrity of welds and joints. In addition, the invention may be used for NDE of surface quality or joint integrity in manufacturing, and has applications to problems presently using radiographic NDE techniques in various fields, such as aviation (cracks in turbine blades, airplane wings, structural joints); aerospace (cracks and welds in rocket engines, fatigue in space shuttle components, such as ceramic tiles); transportation (cracks in bridge abutments); and civil engineering (structural members prone to earthquake damage).

While a specific embodiment has been illustrated and described and specific materials, parameters, etc., have been described, such are not intended to be limiting. Modifications and changes may become apparent to those skilled in the art, and it is intended that the invention be limited only by the scope of the appended claims.

What is claimed is:

1. In a method for detecting cracks and other mechanical and chemical surface anomalies, the improvement comprising:

exposing the surface to short-lived positron-emitting radioactive material for a period of time, removing the materials from the surface so as to leave a residue, detecting back-to-back 511 keV annihilation gamma rays from the surface using a pair of position-sensitive gamma-ray detectors, determining the location of the cracks or surface anomalies, and calculating the width, depth, and length of such cracks or surface anomalies.

2. The method of claim 1, wherein exposing the surface to short-lived radioactive material is carried out by a technique selected from the group consisting of a solution or fluid applied to the surface, aerosol spraying on the surface, high pressure gas, solution, fluid, or spray onto the surface.

3. The method of claim 1 wherein the short-lived radioactive material comprises an isotope selected from the group consisting of $^{11}C$, $^{13}N$, $^{15}O$, and $^{18}F$.

4. The method of claim 1, wherein the short-lived radioactive material is of a molecular form of the isotope selected from the group consisting of $CO_2$, $H_2O$, $CO$, $O_2$, $N_2$, $NO_x$, $NH_3$, and $O_3$.

5. The method of claim 1, wherein determining the location of the cracks or surface anomalies includes detecting coincident gamma-rays.

6. The method of claim 1, additionally including illustrating the width, depth, and length of such cracks and surface anomalies using a Monte Carlo calculation.

7. The method of claim 1, wherein the radioactive material consists of carbon dioxide labeled with $^{11}C$ having a 20.5 minute half-life.

8. A method using Positron Emission Tomography for detecting submicron scale cracks or surface regions of differing chemical reactivity comprising:

providing a surface with short-lived positron-emitting radioactive material, removing excess radioactive material so as to leave partial monolayer, detecting coincident 5 keV annihilation gamma-rays emitted from the surface using a plurality of position-sensitive gamma-ray detectors, reconstructing the source distribution on the emitting surface to determine location and shape of cracks and surface anomalies, and calculating the width, depth, and length thereof.

9. The method of claim 8, wherein providing the short-lived radioactive material is carried out using short-lived isotopes selected from the group consisting of $^{11}C$, $^{13}N$, $^{15}O$, and $^{18}F$.

10. The method of claim 8, wherein providing the short-lived radioactive material is carried out by using a molecular form of the isotope of an oxide layer selected from the group consisting of $CO_2$, $H_2O$, $CO$, $O_2$, $N_2$, $NO_x$, $NH_3$, and $O_3$.

11. The method of claim 8, wherein providing the short-lived radioactive material is carried out using a radioactive gas composed of carbon dioxide labeled with C-11 having a 20.5 minute half-life.

12. The method of claim 8, wherein providing the surface with short-lived radioactive material is carried out by a technique selected from the group consisting of delivery by solution or fluid applied to the surface, delivery by aerosol sprayed on the surface, and delivery by high-pressure gas, solution, fluid, or spray on the surface.

* * * * *